United States Patent
Boulanger

(12) 
(10) Patent No.: US 6,551,296 B1
(45) Date of Patent: *Apr. 22, 2003

(54) SANITARY ABSORBENT ARTICLE WITH POSITIONING TABS INCORPORATING BARRIERS AGAINST LEAKAGE

(75) Inventor: Roger Boulanger, Ste-Julie (CA)

(73) Assignee: Johnson & Johnson Inc., Montreal (CA)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/779,294

(22) Filed: Jan. 6, 1997

(51) Int. Cl.[7] .................................................. A61F 13/15
(52) U.S. Cl. ........................... 604/385.04; 604/385.28; 604/387
(58) Field of Search ............................... 604/385.1, 386, 604/387, 385.2, 385.01, 385.03–385.05, 385.24, 385.28, 389, 391

(56) References Cited

U.S. PATENT DOCUMENTS

| | | | | |
|---|---|---|---|---|
| 3,865,112 A | * | 2/1975 | Roeder ........................ | 604/387 |
| 4,687,478 A | * | 8/1987 | Van Tilburg ................. | 604/387 |
| 5,346,486 A | * | 9/1994 | Osborn et al. ............. | 604/385.1 |
| 5,387,210 A | * | 2/1995 | Murakami ................ | 604/385.1 |
| 5,391,162 A | * | 2/1995 | Widlund et al. ............. | 604/387 |
| 5,447,507 A | * | 9/1995 | Yamamoto ................... | 604/387 |
| 5,490,847 A | * | 2/1996 | Correa et al. ............ | 604/385.1 |
| 5,704,928 A | * | 1/1998 | Morita et al. ................ | 604/387 |
| 5,704,930 A | * | 1/1998 | Louesh et al. .............. | 604/387 |
| 5,807,363 A | * | 9/1998 | Hamajima et al. .......... | 604/387 |
| 5,820,618 A | * | 10/1998 | Roberts et al. ............. | 604/387 |
| 5,921,975 A | * | 7/1999 | Suzuki et al. ............... | 604/387 |

FOREIGN PATENT DOCUMENTS

| | | | |
|---|---|---|---|
| EP | 0 581 258 B1 | 2/1994 | |
| FR | 2 681 242 A1 | 9/1991 | |
| GB | 2 296 445 A | 7/1996 | |
| JP | 5220191 | * 8/1993 | ................ 604/387 |
| JP | 7-24318 | * 5/1995 | ................ 604/387 |
| WO | WO 92/07536 A1 | 5/1992 | |
| WO | WO 93/04651 A1 | 8/1993 | |
| WO | WO 96/23469 A1 | 8/1996 | |

OTHER PUBLICATIONS

Translation of Nasu JP –5220191.*
Australian Patent Office –Search Report–Australian Patent Appln. 50330/98 –dated Jul. 25, 2000.
Norwiegian Patent Office –Search Report –Norwegian Patent Application 1998 dated 0035 Aug. 14, 2000.
EP Patent Office –Search Report –EP Application No. 98100075.5 –dated Sep. 8, 1999.

* cited by examiner

Primary Examiner—John G. Weiss
Assistant Examiner—Jamisue Webb

(57) ABSTRACT

A sanitary absorbent article is provided which has a generally rectangular main body and two positioning tabs laterally extending from the main body for use in securing the article to an undergarment of a user. The tabs, when folded, provide upstanding barriers that extend along the longitudinal edges of the main body to prevent leakage of menstrual fluid.

17 Claims, 3 Drawing Sheets

SANITARY ABSORBENT ARTICLE WITH POSITIONING TABS INCORPORATING BARRIERS AGAINST LEAKAGE

FIELD OF THE INVENTION

The present invention relates to a sanitary absorbent product, such as a sanitary napkin or urinary protection article, which is worn in contact with the skin of the wearer for the purpose of absorption and holding of body liquids and, more particularly, to an absorbent product having laterally extending tabs for attachment to the undergarment of the wearer. The tabs feature barrier devices for preventing leakage.

BACKGROUND OF THE INVENTION

A typical tabbed sanitary napkin includes a central absorbent body, and two or more positioning tabs extending laterally outward from the longitudinal edges of the central absorbent body which are adapted to be wrapped around the edges of the crotch portion of a wearer's undergarment to hold the sanitary napkin in place. A problem with early designs for sanitary napkins with tabs is that when the tabs are pulled into place, there is a tendency for fluid to wick along the surface of the tabs where it can stain the wearer's outer clothing since there is no effective barrier against leakage along the side of the napkin. Moreover, when the tabs are pulled into place, the body facing surface of the central absorbent body has a tendency to slope away from the user in the region adjacent the tabs, thus making side leakage more likely to occur in this area.

Various attempts to curb lateral leakage near the tabs have been tried. For example, U.S. Pat. No. 5,391,162 discloses a sanitary napkin with tabs secured in a face-to-face relationship with the back of the napkin. This arrangement allows upstanding barriers to form when the tabs are longitudinally tensioned, the barriers pivoting from their initial flat position to an upstanding position. The deployment of the upstanding barriers depends on accurate placement and correct sizing of the napkin with respect to the user's undergarment. The fact that the barriers extend substantially along the entire length of the body of the napkin makes the product bulkier and less comfortable. In addition, the correct functioning of this design depends upon accurate installation. In a second embodiment disclosed in the same patent and having similar disadvantages, loops in the non-absorbent layers are provided, running the length of the main body of the napkin, with the main purpose of preventing the flow of liquid into the material in the tabs.

U.S. Pat. No. 5,387,210 suggests an elaborate process of folding the top layer of the tabs whereby side barriers rise when the tabs are folded about the edges of the panty. A disadvantage of this design is that a more complex manufacture process is required. Moreover, a separate piece of material is required to form the top layer of each tab, independent of the top layer of the central absorbent body. Also, unless the fit of the napkin is correct, the side barriers which are supposed to rise may be forced against the skin of the user and be unable to rise when the tabs are pulled.

European patent application published in February 1994 with publication number 0 581 258 A1 discloses a sanitary napkin with positioning tabs. Each tab has an inwardly projecting portion that extends over the cover layer to form a barrier device and an outwardly projecting portion for use in attaching the napkin to the undergarment of the wearer. In manufacture, separate pieces are required for the positioning tabs and the main body, resulting in a more expensive process. Furthermore, as with U.S. Pat. No. 5,387,210, the potential exists for the side barriers to be pressed against the user, and be rendered ineffective.

SUMMARY OF THE INVENTION

It is an object of the present invention to provide a sanitary absorbent product with positioning tabs, which obviates or mitigates the aforementioned disadvantages.

It is another object of this invention to provide a novel sanitary absorbent product which provides protection against lateral leakage using barriers which are located and formed in a unique manner so as to simplify manufacture and use.

As embodied and broadly described herein, the present invention provides a sanitary absorbent product comprising a layered elongate main body, said main body having two opposed longitudinal edges, two positioning tabs extending laterally from said main body, each positioning tab having a width and a length, the width being substantially parallel to the longitudinal edges of the main body and the length being substantially perpendicular to the longitudinal edges of the main body. In a preferred embodiment, the width of the tab does not exceed 50% of the length of said main body. Each positioning tab is provided with a side barrier device which projects from a body-facing surface of the positioning tab, said barrier device being integrally formed with the respective positioning tab. It is preferred that the barrier device have a length which does not substantially exceed the width of the tab. Accordingly, the length of the barrier device is substantially shorter than the length of said main body.

In a most preferred embodiment, the sanitary absorbent product is a sanitary napkin that includes an absorbent core held captive between a liquid permeable cover layer and a liquid impervious barrier layer. The cover layer and the barrier layer are provided with co-extensive lateral projections that are peripherally sealed to one another by adhesive or thermal bonding to form the positioning tabs. Optional adhesive zones may be provided on the barrier layer portions of the positioning tabs to allow the tabs to adhere to the garment facing surface of the undergarment of the wearer.

A transverse fold is formed on each positioning tab to provide a barrier function against side leakage. The fold is generally parallel to the longitudinal axis of the sanitary napkin and is located at the interface or juncture of the main body and the positioning tab. In use, when the positioning tab is tensioned and folded around the edge of the panty, the upper surface of the tab (materialized by the lateral projection of the cover layer) acquires a sloping configuration in the region near the boundary of the main body. The fold, however, projects upwardly from the sloping surface and behaves as a barrier, preventing menstrual fluid from escaping and staining the wearer's clothes. Thus, the ability of the fold to withstand the tension forces exerted on the positioning tab, that cause the tab to incline downwardly, without flattening or otherwise losing its three-dimensional character, substantially reduces the likelihood of failure.

As embodied and broadly described herein, the invention also provides a sanitary absorbent product comprising:
  a layered elongate main body, comprising from top layer to bottom layer a cover layer which is permeable to liquid, at least one absorbent layer and a barrier layer which is impermeable to liquid, said main body having two opposed longitudinal edges and two opposed lateral edges;
  two positioning tabs extending laterally from said main body intermediate said lateral edges, each positioning tab comprising a barrier layer portion continuous with the barrier layer of said main body, and a cover layer portion continuous with the cover layer of said main body;

an adhesive means provided on the barrier layer portion of each positioning tab for attachment of the tab to a garment facing surface of an undergarment;

the barrier layer portion of each positioning tab being bonded to the cover layer portion of the tab around the perimeter of the tab; and an upwardly projecting barrier formed along each interface between said positioning tabs and said main body, said upwardly projecting barrier having a length not substantially exceeding a width of a respective positioning tab at said interface, each positioning tab having a maximal width not substantially exceeding 50% of a maximal length of said main body.

As embodied and broadly described herein, the invention also provides a sanitary absorbent product comprising:

an elongate main body, said main body having two opposed longitudinal edges;

a positioning tab extending laterally from each longitudinal side edge of said main body, each positioning tab including:
  a) a main tab element extending laterally from a respective longitudinal side of said main body;
  b) a secondary tab element projecting from said main tab element from a location thereon that is outwardly removed from a respective longitudinal edge of said main body;
  c) an adhesive means provided on said secondary tab element for attachment of the positioning tab to a garment facing surface of an undergarment of a wearer, whereby a region of said main tab element extending beyond said location tends to prevent lateral leakage of liquid exuded by the wearer.

As embodied and broadly described herein, the invention further provides a method of making a sanitary absorbent product, said method comprising the steps of:

providing an absorbent layer having two opposed longitudinal edges and two opposed lateral edges, said absorbent layer having a longitudinal axis;

providing a permeable cover layer and an impermeable barrier layer of substantially the same dimensions, such that said cover layer and said barrier layer possess a main body slightly larger in length and width than said absorbent layer, and two laterally extending positioning tabs, each tab having a maximal width not exceeding substantially 50% of a maximal length of said main body;

sandwiching said absorbent layer between said cover layer and said barrier layer;

bonding said cover layer to said barrier layer along the lateral edges of the main body, and along the perimeter of the positioning tabs; and folding the positioning tabs to form two upwardly projecting barriers.

As embodied and broadly described herein, the invention also provides a method of making a sanitary absorbent product, said method comprising the steps of:

providing an absorbent layer having two opposed longitudinal edges and two opposed lateral edges, said absorbent layer having a longitudinal axis;

providing a permeable cover layer and an impermeable barrier layer to substantially the same dimensions, such that said cover layer and said barrier layer possess a main body slightly larger in length and width than said absorbent layer, and two laterally extending positioning tabs;

sandwiching said absorbent layer between said cover layer and said barrier layer; and bonding to each positioning tab a secondary positioning tab along a line of juncture outwardly removed from a longitudinal edge of said main body, said line of juncture extending along said longitudinal edge.

BRIEF DESCRIPTION OF THE DRAWINGS

The invention will now be described in greater detail with reference to the accompanying drawings, in which.

DETAILED DESCRIPTION OF THE INVENTION

Figure 1:
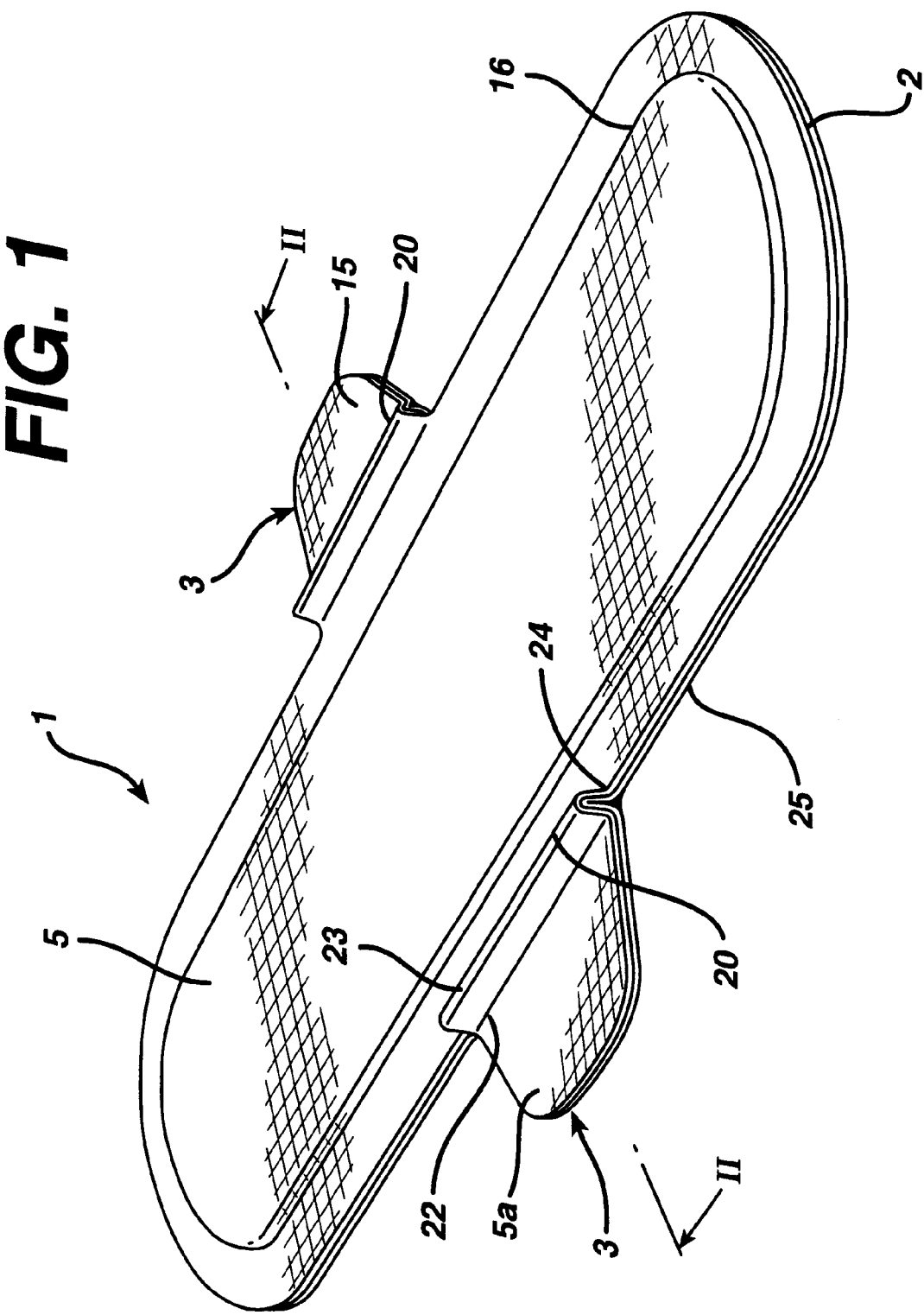
FIG. 1 is a plan view of a sanitary napkin constructed according to a first aspect of the invention.
Figure 2:
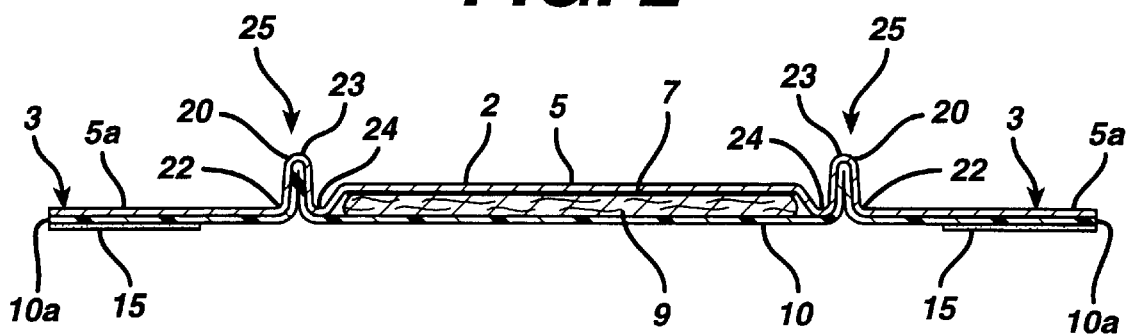
FIG. 2 is a sectional view of the sanitary napkin taken on line II—II of FIG. 1.
Figure 3:
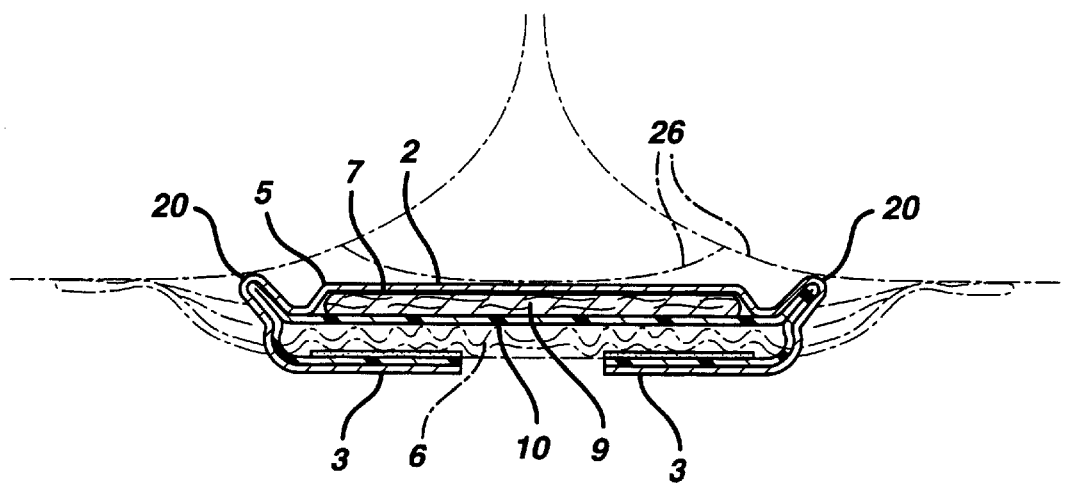
FIG. 3 is a sectional view of the sanitary napkin of FIG. 1 in the configuration it would attain when in use.

Referring firstly to FIGS. 1, 2 and 3, a sanitary napkin 1 according to a first broad aspect of the invention is shown comprising an elongate main body 2 with two laterally extending positioning tabs 3. The main body 2 is made in a layered manner and includes from the top down a cover layer 5, an optional transfer layer 7, an absorbent layer 9, and a barrier layer 10. Each positioning tab 3 has a barrier layer portion 10a that is continuous with the barrier layer 10 of the main body 2 and a cover layer portion 5a which is continuous with the cover layer 5 of the main body 2. The barrier layer portions 10a are provided with adhesive patches 15 for securing the positioning tabs to the outside of an undergarment 6. As is conventional, silicon coated paper (not shown) is provided as a temporary protective cover for the adhesive patches 15.

The cover layer 5 is a permeable layer of woven or nonwoven fabric or alternatively, the cover layer may be made from apertured polymeric film.

The optional transfer layer 7, which may be made of cellulose fibers, synthetic fibers, or combinations thereof, and generally has a high void volume porous structure which is capable of fast liquid acquisition. The ability of the transfer layer to take-up liquid rapidly prevents the body exudate from pooling on the cover layer, thus minimizing any discomfort to the user. This feature also reduces the likelihood of body exudate from leaking past the side edges of the sanitary napkin. The transfer layer 7 is glued to the cover layer 5 above and to the absorbent layer 9 below.

The absorbent layer 9, which may be made of cellulose fibers, sphagnum moss or combinations thereof, optionally with super absorbent polymers, provides for the actual absorption of the collected fluid. The transfer layer 7 provides quick transfer of liquid from the surface of the napkin to the absorbent layer 9, where a slower absorptive process takes place. The liquid is initially absorbed near the place where it has come through the transfer layer 7, but subsequently spreads itself out somewhat uniformly within the absorbent layer 9.

The barrier layer 10 which may be made of polyethylene is below the absorbent layer 9 and is impermeable to liquid. Thus, liquid collected by the absorbent layer 9 is not allowed to flow on further to the user's undergarment 6.

In manufacturing the napkin 1, the barrier layer 10 and the cover layer 5 are cut to substantially the same size, with elongate main areas which are slightly wider and longer than the transfer layer 7 and the absorbent layer 9, and with two laterally extending portions adapted to form positioning tabs 3 as discussed above. The napkin 1 is sealed around the edges with a continuous thermal bond 16 between the barrier layer 10 and the cover layer 5. This forms a flange seal extending along the perimeter of the main body 2 where the barrier 10 and cover layers 5 extend beyond the other main body layers. The flange seal includes a pair of opposite rectilinear portions located on respective longitudinal sides of the napkin from which the tabs 3 originate. In a preferred embodiment, the flange seal is formed along the peripheral edge margins of the absorbent layer 9 adjacent the body-facing side of the absorbent layer 9, such that the tabs extend laterally outward from the longitudinal edges of the napkin and are in substantially the same plane as the cover layer 5. The barrier layer and the cover layer are also sealed along the outer perimeter of the tabs 3. Side barriers 20 are formed in each respective tab by performing three bends 22,23,24 on each tab as illustrated, the bends being parallel to the longitudinal edges 25 of the elongate main body 2 and adjacent the edge of the absorbent layer 9. Note that since the side barriers 20 are integrally formed from the positioning tabs 3, the length of the side barriers 20 is generally the same as the width as the tabs. The length of the positioning tabs and concommittantly the height of the barriers 20 may vary in accordance with the intended application. Preferably, the barriers 20 have the same length as the width of the tabs (the width of a tab is measured along at the base of the tab where it joins the flange seal along a direction generally parallel to a longitudinal axis of the napkin 1.) Most preferably, the barriers 20 have a length in the range from about 2 to about 4 inches.

The barriers 20 are parallel and immediately adjacent to the portions of the flange seal located at a proximal end of the respective tabs 3.

Each barrier 20 preferably has a permanent shape which is achieved by adhering a segment of the tab between the bends 22–23 to an adjacent segment of the tab defined between the bends 24 to 23. The two segments are folded at fold region 25 to form an apex, and wherein the two segments are brought together in a facing arrangement, and then bonded to one another by adhesive or thermal bonding. A characterizing element of the invention is the fact that the segments are integrally formed with the positioning tab 3 and they are continuous with one another. More specifically, the segments connect at the apex portion of the barrier 20 to provide each side barrier device with a single continuous surface.

In a particularly preferred embodiment, the adhesive patch 15, normally provided for bonding the tab 3 to the undergarment of the wearer may be used to secure the two segments together. By forming each fold region 25 within the boundary of the adhesive patch 15, a portion of the patch is utilized to bond the segments between the bends 22,23,24 while the remaining portion is used to adhere the positioning tab 3 to the undergarment of the wearer. More specifically, the manufacturing process consists of applying the adhesive patch 15 to the positioning tab and bend the tab as described above to create the barrier 20. Silicone coated release paper is then applied to the exposed portion of the adhesive patch that still remains and that will be used to bond the tab to the undergarment. To avoid weakening the bond positioning tab/undergarment, the adhesive patch 15 should be made larger to compensate for the loss of adhesive surface due to folding-up of the positioning tab 3 to form the barrier layer 20.

In traditional designs, when the positioning tabs are pulled into place, the main absorbent body attains a convex surface cross-section near the positioning tabs, sloping away from the user, which tends to cause some flow of liquid toward the edges of the napkin resulting in leakage. The barriers 20 in the current embodiment of the invention tend to prevent the leakage of liquid which has flowed toward the edges near the positioning tabs 3 by providing the capacity to block lateral flow beyond these barriers. It should be appreciated that the barriers 20 are strategically placed where leakage is most likely to occur, i.e., in the region of the sloping tabs. Thus, the barriers 20 are effective while remaining relatively small which avoid the discomfort to the user that may result from longer barriers running the full length of the product.

The manner in which the napkin is used will now be described with particular reference to FIG. 3. First, if the main body portion is provided with adhesive, the release paper covering such adhesive zones is removed. The napkin 1 is then placed in the crotch area of the inner side of the user's undergarment 6 and the adhesive is secured to the undergarment. The silicon coated papers are then peeled off from the positioning tabs 3 exposing the adhesive patches 15 on the positioning tabs 3. The positioning tabs 3 are folded around and secured to the outer surface of the crotch area of the undergarment 6 with the adhesive patches 15. The folding of the positioning tabs 3 may cause some displacement of the side barriers 20 from the generally vertical position illustrated in FIG. 2 to a sloping position illustrated in FIG. 3. The distal ends of the barriers 20 are adapted to fit snugly against the body as illustrated schematically by dotted line 26. Fluid which is exuded by the user is first collected by the transfer layer 7 which functions to wick the liquid away quickly from the user's skin. Then absorption and subsequent storage of most of the liquid by the absorptive layer 9 occurs. Some liquid may fail to be absorbed and may flow toward the side of the napkin 1. This usually will occur near the center of the longitudinal axis of this where most of the flow originates and also because the surface of the napkin slopes due to the tension in the positioning tabs 3. Liquid which makes it all the way to the side of the napkin will be prevented from leaking beyond the side barriers 20 which were formed adjacent to the positioning tabs 3, thereby preventing the liquid from staining the user's undergarment.

Figure 4:
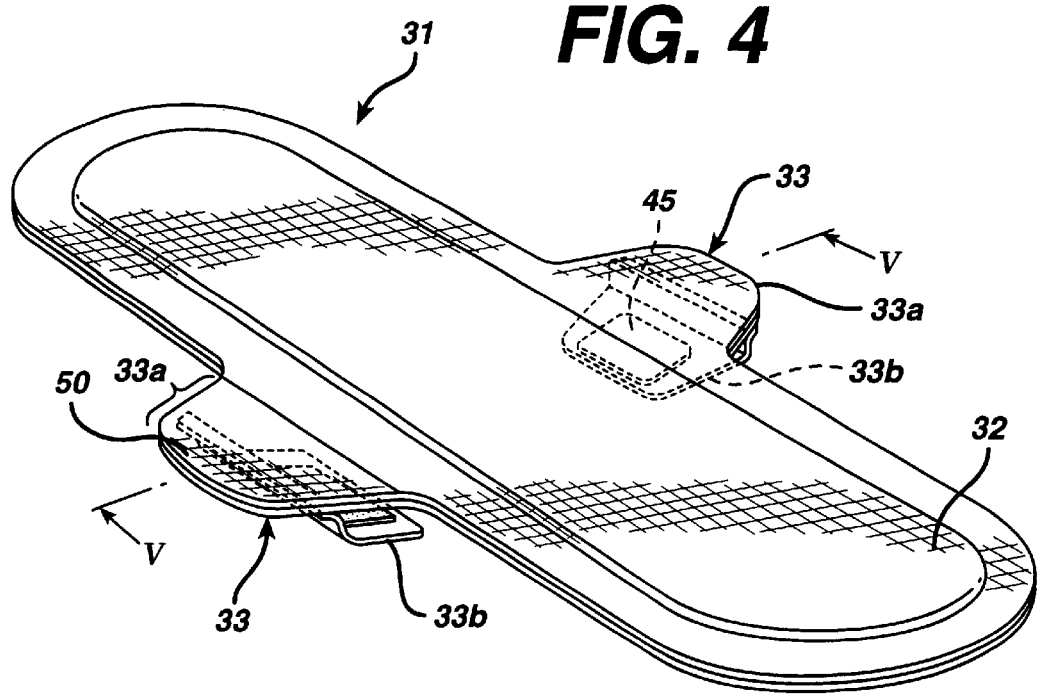
FIG. 4 is a plan view of a sanitary napkin according to a second aspect of the invention.
Figure 5:
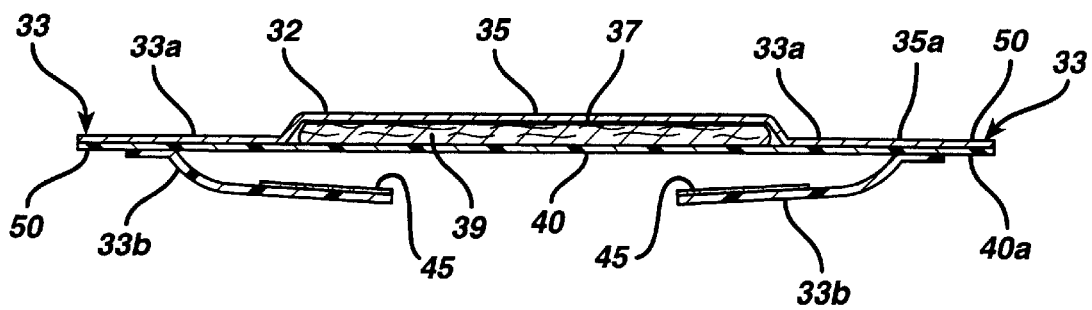
FIG. 5 is a sectional view of the sanitary napkin taken on line V—V of FIG. 4.

Referring now to FIGS. 4 and 5, a sanitary napkin 31 according to a second broad aspect of the invention is shown comprising an elongate main body 32 with two laterally extending compound positioning tabs 33. The main body 32 is made in a layered manner as discussed above for the first embodiment, having a cover layer 35, transfer layer 37, absorbent layer 39 and barrier layer 40. Each positioning tab 33 has a main tab element 33a that projects laterally from the side of the main body 32. The main tab element 33a includes a barrier layer portion 40a which is continuous with the barrier layer 40 of the body 32 and a cover layer portion 35a which is continuous with the cover layer 35 of the body 32. The positioning tab 33 also includes a secondary tab element 33b originating from the undersurface of the main tab element 33a and projecting inwardly (toward the main body 32). The secondary tab element 33b is glued or heat-sealed to the main tab element 33a in a line parallel, but a short distance away from the longitudinal edges of the main body 32. An adhesive patch 45 is formed on the secondary tab element 33b for attachment to the garment facing surface of an undergarment (not shown). Typically, the adhesive patch 45 will be covered with a protective silicone coated release paper that is peeled off immediately before installing the absorbent product.

The secondary tab element 33b may be made of any convenient material, possibly but not necessarily being the same as used for the main tab element 33a.

In manufacturing the napkin 31, the main body and laterally extending positioning tabs 33 are manufactured as before, but without the application of adhesive to the laterally extending main positioning tabs elements 33a. Instead, adhesive patches 45 are applied to the upper surface of the secondary tab elements 33b.

As indicated above, the secondary tab elements 33a have adhesive patches 45 such that when these positioning tabs elements are wrapped around the edges of the undergarment, they may be adhered to the outer side of the undergarment and thereby provide security for the placement of the napkin 31. In traditional designs, when the positioning tabs are pulled into place, the main absorbent body attains a convex surface cross-section near the positioning tabs, sloping away from the user, which tends to cause some flow of liquid toward the edges of the napkin resulting in leakage. When the positioning tabs 33 are pulled to be secured to the undergarment, little or no tension is applied to the free edge portion 50 (the portion defined between the line of juncture of the main tab elements 33a and the respective secondary tab element) of each tab that behaves as a barrier and essentially retains its erect position, resisting the sloping effect obtained in traditional designs. The barriers 33 in the current embodiment of the invention also tend to prevent the leakage of liquid which has flowed toward the edges near the positioning tabs 33 by providing the capacity to block lateral flow beyond these barriers.

The manner in which the napkin according to the second aspect is to be used is the same in essence to that described for the first embodiment.

The scope of the present invention is not limited by the description, examples and suggestive uses herein, as modifications can be made without departing from the spirit of the invention. Thus, it is intended that the present application covers the modifications and variations of this invention provided they come within the scope of the appended claims and their equivalents.

What is claimed is:

1. A sanitary absorbent product comprising a layered elongate main body including a liquid permeable cover layer, an absorbent core and a liquid impermeable barrier layer, said absorbent core being located between said cover layer and said barrier layer, said main body having two opposed longitudinal edges, said longitudinal edges defining a length of the sanitary absorbent product, a positioning tab extending laterally from each of said longitudinal edges of said main body, each positioning tab having a width and a length, the width being substantially parallel to the longitudinal edges of said main body and does not exceed 50% of the length of the main body, each positioning tab including a cover layer portion continuous with said cover layer of said main body and a barrier layer portion continuous with said barrier layer of said main body, each positioning tab having a side barrier device projecting from a body facing surface of each said positioning tab, said barrier device being continuous and integrally formed from the cover layer and barrier layer of the respective positioning tab, and wherein said barrier device has a length which does not substantially exceed the width of said positioning tab.

2. The sanitary absorbent product according to claim 1 wherein the side barrier device is formed from segments of the positioning tab, said segments being joined to one another in a face-to-face relationship.

3. The sanitary absorbent product according to claim 2, wherein said segments are continuous.

4. The sanitary absorbent product according to claim 3, wherein said barrier device includes an apex portion establishing continuity between said segments.

5. The sanitary absorbent product according to claim 3, wherein said segments extend transversely with relation to said positioning tab.

6. The sanitary absorbent product according to claim 5, wherein said segments are generally parallel to a longitudinal edge of said main body.

7. The sanitary absorbent product according to claim 2, wherein said segments are bonded to one another by means of adhesive.

8. The sanitary absorbent product according to claim 2, wherein said positioning tab includes an adhesive zone for bonding said positioning tab to an undergarment of a wearer, said adhesive zone being formed on a surface of said positioning tab that is opposite a surface of said positioning tab from which said barrier device projects, said barrier device intercepting a boundary of said adhesive zone.

9. The sanitary absorbent product according to claim 1, wherein said cover layer and said barrier layer are bonded to one another along an area adjacent to said barrier device.

10. The sanitary absorbent product according to claim 1, wherein said cover layer and said barrier layer are bonded to one another to form a peripheral flange seal, the side barrier device on each tab being immediately adjacent said flange seal and extending generally parallel to a portion of said flange seal that spans a length of the tab.

11. The sanitary absorbent product according to claim 1, wherein said product is selected from the group consisting of sanitary napkin and urinary protection article.

12. The sanitary absorbent product as defined in claim 10, wherein each tab has a length in the range from about 2 inches to about 4 inches.

13. A sanitary absorbent product comprising:
   a layered elongate main body, comprising from top layer to bottom layer a cover layer which is permeable to liquid, at least one absorbent layer and a barrier layer which is impermeable to liquid, said main body having two opposed longitudinal edges and two opposed lateral edges;
   a positioning tab extending laterally from each longitudinal edge of said main body intermediate said lateral edges, each positioning tab comprising a barrier layer portion continuous with the barrier layer of said main body, and a cover layer portion continuous with the cover layer of said main body;
   an adhesive means provided on the barrier layer portion of each positioning tab for attachment of the tab to a garment facing surface of an undergarment;
   the barrier layer portion of each positioning tab being bonded to the cover layer portion of the tab around the perimeter of the tab; and
   an upwardly projecting barrier device formed along each interface between said positioning tabs and said main body, said upwardly projecting barrier device being continuous and integrally formed from the cover layer and barrier layer of the respective positioning tab and having a length not substantially exceeding a width of a respective positioning tab at said interface, each positioning tab having a maximal width not substantially exceeding 50% of a maximal length of said main body.

14. The sanitary absorbent product according to claim 13, wherein said upwardly projecting barrier includes two segments integrally formed with said positioning tab, said segments being joined to one another in a face-to-face relationship, said upwardly projecting barrier including an apex portion establishing continuity between said segments.

15. The sanitary absorbent product according to claim 14, wherein said segments extend transversely with relation to said positioning tab and are generally parallel to a longitudinal edge of said main body.

16. The sanitary absorbent product according to claim 14, wherein said segments are bonded to one another by means of adhesive.

17. The sanitary absorbent product according to claim 13, wherein said product is selected from the group consisting of sanitary napkin and urinary protection article.

* * * * *